(12) United States Patent
Niazi et al.

(10) Patent No.: US 10,344,280 B1
(45) Date of Patent: Jul. 9, 2019

(54) COMPOSITIONS AND METHODS FOR REDUCTION OF ALLOGRAFT RECOGNITION AND REJECTION

(71) Applicant: Nant Holdings IP, LLC, Culver City, CA (US)

(72) Inventors: Kayvan Niazi, Los Angeles, CA (US); Shahrooz Rabizadeh, Los Angeles, CA (US); Patrick Soon-Shiong, Los Angeles, CA (US)

(73) Assignee: NANT HOLDINGS IP, LLC, Culver City, CA (US)

(*) Notice: Subject to any disclaimer, the term of this patent is extended or adjusted under 35 U.S.C. 154(b) by 52 days.

(21) Appl. No.: 15/682,977

(22) Filed: Aug. 22, 2017

Related U.S. Application Data

(62) Division of application No. 14/992,861, filed on Jan. 11, 2016, now Pat. No. 9,765,330.

(60) Provisional application No. 62/167,811, filed on May 28, 2015, provisional application No. 62/101,653, filed on Jan. 9, 2015.

(51) Int. Cl.
*A61K 48/00* (2006.01)
*C12N 15/113* (2010.01)
*C12N 5/0783* (2010.01)

(52) U.S. Cl.
CPC ......... *C12N 15/113* (2013.01); *C12N 5/0638* (2013.01); *C12N 5/0646* (2013.01); *C12N 2310/14* (2013.01); *C12N 2510/00* (2013.01)

(58) Field of Classification Search
CPC ................................................ A61K 48/0066
See application file for complete search history.

(56) References Cited

U.S. PATENT DOCUMENTS

| | | | |
|---|---|---|---|
| 6,410,721 | B1 | 6/2002 | Hunt et al. |
| 6,514,752 | B1 | 2/2003 | Kucherlapati et al. |
| 2004/0225112 | A1 | 11/2004 | Crew |
| 2013/0078243 | A1 | 3/2013 | Ibrahim |

FOREIGN PATENT DOCUMENTS

| | | |
|---|---|---|
| WO | 1995-17911 | 7/1995 |
| WO | 2010-052228 A1 | 5/2010 |

OTHER PUBLICATIONS

Mannon, R.B., et al., "Absence of Donor MHC Antigen Expression Ameliorates Chronic Kidney Allograft Rejection," Kidney International, vol. 62 (2002), pp. 290-300.

*Primary Examiner* — Rosanne Kosson
(74) *Attorney, Agent, or Firm* — Umberg/Zipser LLP

(57) ABSTRACT

Allograft recognition and rejection of donor cells in a host is reduced by limiting or even abrogating expression of the donor cell's MHC-I peptides to avoid CD8+ T-cell recognition and by expression of inhibitory factors to avoid an NK cell mediated cytotoxic response.

14 Claims, 2 Drawing Sheets

Specification includes a Sequence Listing.

1528

Control

Human β-2 microglobulin shRNA sequences:
1528-AAGAGTTCAAATCTGACCAAGGTTTTGGCCACTGACTGACCTTGGTCATTTGAACTCTT
Control-ATCAAAGCCTTGCAGGTAATGGTTTTGGCCACTGACTGACCATTACCTAAGGCTTTGAT

SEQUENCE LISTING

```
<160> NUMBER OF SEQ ID NOS: 4

<210> SEQ ID NO 1
<211> LENGTH: 984
<212> TYPE: DNA
<213> ORGANISM: Homo sapiens
```

```
<400> SEQUENCE: 1
aatataagtg gaggcgtcgc gctggcgggc attcctgaag ctgacagcat tcgggccgag      60
atgtctcgct ccgtggcctt agctgtgctc gcgctactct ctctttctgg cctggaggct     120
atccagcgta ctccaaagat tcaggtttac tcacgtcatc cagcagagaa tggaaagtca     180
aatttcctga attgctatgt gtctgggttt catccatccg acattgaagt tgacttactg     240
aagaatggag agagaattga aaaagtggag cattcagact tgtctttcag caaggactgg     300
tctttctatc tcttgtacta cactgaattc accccactg aaaagatga gtatgcctgc       360 cgtgtctttg tgactttgtc acagcccaag atagttaagt gggatcgaga catgtaagca     420
gcatcatgga ggtttgaaga tgccgcattt ggattggatg aattccaaat tctgcttgct     480
tgctttttaa tattgatatg cttatacact tacactttat gcacaaaatg tagggttata     540
ataatgttaa catggacatg atcttcttta taattctact ttgagtgctg tctccatgtt     600
tgatgtatct gagcaggttg ctccacaggt agctctagga gggctggcaa cttagaggtg     660
gggagcagag aattctctta ccaacatca acatcttggt cagatttgaa ctcttcaatc      720
tcttgcactc aaagcttgtt aagatagtta agcgtgcata agttaacttc caatttacat     780
actctgctta gaatttgggg gaaaatttag aaatataatt gacaggatta ttggaaattt     840
gttataatga atgaaacatt ttgtcatata agattcatat ttacttctta tacatttgat     900
aaagtaaggc atggttgtgg ttaatctggt ttattttgt tccacaagtt aaataaatca      960
taaaacttga tgtgttatct ctta                                            984

<210> SEQ ID NO 2
<211> LENGTH: 59
<212> TYPE: DNA
<213> ORGANISM: Homo sapiens

<400> SEQUENCE: 2
aagagttcaa atctgaccaa ggttttggcc actgactgac cttggtcatt tgaactctt       59

<210> SEQ ID NO 3
<211> LENGTH: 59
<212> TYPE: DNA
<213> ORGANISM: Artificial Sequence
<220> FEATURE:
<223> OTHER INFORMATION: Synthetic nucleic acid

<400> SEQUENCE: 3
atcaaagcct tgcaggtaat ggttttggcc actgactgac cattacctaa ggctttgat       59

<210> SEQ ID NO 4
<211> LENGTH: 843
<212> TYPE: DNA
<213> ORGANISM: Artificial Sequence
<220> FEATURE:
<223> OTHER INFORMATION: Synthetic plasmid

<400> SEQUENCE: 4
ttggcaccaa aatcaacggg actttccaaa atgtcgtaac aactccgccc cattgacgca      60
aatgggcggt aggcgtgtac ggtgggaggt ctatataagc agagctctct ggctaactag     120
agaacccact gcttactggc ttatcgaaat taatacgact cactataggg agtcccaagc     180
tggctagtta agctatcaac aagtttgtac aaaaaagcag gctttaaagg gaggtaggag     240
tcgaccagtg gatcctggag gcttgctgaa ggctgtatgc tgaagagttc aaatctgacc     300
aaggttttgg ccactgactg accttggtca tttgaactct tcaggacaca aggcctgtta     360
```

```
ctagcactca catggaacaa atggcccaga tctggccgca ctcgagatat ctagacccag    420
ctttcttgta caaagtggtt gatctagagg gcccgcgttc gctgatgggg gaggctaact    480
gaaacacgga aggagacaat accggaagga acccgcgcta tgacggcaat aaaaagacag    540
aataaaacgc acgggtgttg ggtcgtttgt tcataaacgc ggggttcggt cccagggctg    600
gcactctgtc gatacccac cgtgacccca ttggggccaa tacgcccgcg tttcttcctt    660
ttccccaccc cacccccaa gttcggggtg aaggcccagg gctcgcagcc aacgtcgggg    720
cggcaggccc tgccatagca tccctatag tgagtcgtat tacatggtca tagctgtttc    780
ctggcagctc tggcctgtgt ctcaaaatct ctgatggatc tgcgcagctg gggctctagg    840
ggg                                                                 843
```

COMPOSITIONS AND METHODS FOR REDUCTION OF ALLOGRAFT RECOGNITION AND REJECTION

This application claims priority to and is a divisional of U.S. application Ser. No. 14/992,861, filed Jan. 11, 2016, which claimed priority to U.S. provisional application Ser. No. 62/101,653, filed on Jan. 9, 2015, and 62/167,811, filed on May 28, 2015, all of which are incorporated by reference herein.

FIELD OF THE INVENTION

The field of the invention is genetic engineered cells with altered histocompatibility and methods therefor, especially as it relates to genetic modifications of such cells to thereby reduce allograft recognition by $CD4^+$, $CD8^+$, and/or NK cells.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The mammalian immune system comprises innate and adaptive immune cells operating in concert to recognize and remove damaged, infected, or otherwise diseased cells and/or tissues. This is accomplished through a complex sequence of events using sensory pathways to identify affected tissues (typically via innate immune cells such as monocytes/macrophages, dendritic cells, and natural killer or NK cells) and effector cells and/or their products (typically T- and B-lymphocytes, antibodies, etc.) to not only eradicate targeted tissues but also form an exquisitely specific immunological memory against the offending agent.

Increasing knowledge of the molecular events surrounding immune activation has led to the creation of ever more active vaccines that in turn provide protection against an increasing array of pathogens. For example, early vaccine formulations have focused on stimulating host B-cells to produce protective antibodies, while more recent vaccine formulations attempt to target cancer cells for recognition by host CD8+ cytotoxic T cells and subsequent destruction. Conversely, other attempts aimed to induce tolerance via CD4+ T cell recognition of "self" or inert antigens to treat autoimmune diseases or allergic reactions. Notably, and common to most, if not all of the targeted responses of the immune system to an offending antigen are recognition events mediated between MHC-complexes on affected cells and T-cell receptors on specific T-cells in the cellular immune response, particularly CD8+ and CD4+ cells.

Human CD8+ T cell activation generally requires recognition of a tri-molecular complex of proteins on the surface of target cells composed of a classical MHC-I heavy chain (e.g. HLA-A, -B, or -C in man), a non-covalently bound β-2 microglobulin (β-2m) light chain, and a short peptide (typically 8-11 amino acids) that is derived from proteosomal degradation of cytoplasmic proteins. Like most cellular macromolecules, cytoplasmic proteins exhibit unique half-lives, and "older" proteins are degraded and turned over by the proteasome complex into short peptides. These peptides are transferred to the lumen of the ER by the TAP1/2 complex where they are loaded onto the classical MHC-I heavy chain/β-2m complexes and 'quality controlled' by accessory proteins like tapasin. Once appropriately loaded, these complexes traffic through the Golgi apparatus to the cell surface where they interact with T cell receptors (TCR) of circulating CD8+ T cells.

Unlike CD8+ T cells, CD4+ T cells recognize a tri-molecular complex of surface proteins composed of α and β chains of MHC-II (HLA-DR, DP, and DQ α and β loci in man) and bound peptides (typically 12-20 amino acids). Unlike MHC-I, MHC-II is significantly more restricted in its expression (e.g., limited to antigen presenting cells like monocytes/macrophages, dendritic cells, and B-cells) and MHC-II associated peptide epitopes are often derived from extracellular or endosomal sites and not the cytoplasm.

Despite many advances in creating antigen-specific protective immune responses against foreign or otherwise offending antigens through immunization, inhibition of undesired antigen specific immune responses remains a difficult task. This is particularly apparent in tissue transplantation where suppression of tissue rejection is generally limited to immunosuppressive therapy (e.g., via corticosteroids, mTOR and/or calcineurin inhibitors, etc.), antibody therapy, or bone marrow transplant. However, such therapies are often fraught with undesirable side effects and tend to only incompletely protect the allograft. In addition, use of immunosuppressive agents compromise the recipient's immune system, frequently with disastrous consequences. Therefore, success of allograft transplants most heavily relies on HLA-based tissue type matching.

Mechanistically, allograft rejection is predominantly effected by the recipient's CD8+ cytotoxic T cells via recognition of the grafted cells'/tissue's foreign MHC-I proteins. In addition, CD4+ T cells can also recognize allografts where they express foreign MHC class II (like HLA-DR). To complicate matters further, pre-existing serum antibodies specific for graft proteins can also lead to graft rejection. By some estimates, 1-10% of a recipient's T cells recognize and respond to allografts, destroying grafts within days to weeks in a peptide epitope-independent manner, while T cell antigen recognition of typical antigens is restricted by the host's particular haplotype of MHC-I or -II and specific for the bound peptide under normal immunological conditions (with antigen-specific T cell frequencies numbering many powers of ten less than their alloreactive counterparts in antigen naïve hosts). This intrinsic reactivity to foreign cells necessitates tissue matching between donors and recipients across the HLA loci (and in particular, HLA-A, HLA-B, and HLA-DR proteins) and is generally deemed critical to graft acceptance.

It should be appreciated that normal biological conditions exist where certain cells evade CD8+ T cell recognition, including neurons and an embryo's trophoblast cells during pregnancy (as recognition of the father's "alloantigens" would lead to destruction of the embryo). Altered expression or function of proteins required for MHC-I antigen processing/presentation is also noted in many varieties of cancer cells, which use this mechanism to avoid detection of cancer neo-antigens by CD8+ T cells, and in certain viral infections via expression of viral proteins like human herpesvirus 1

(HHV-1) ICP47, cytomegalovirus (CMV) unique short region proteins US2, US3, US6, and US11, etc.

Unfortunately, attempting to employ a similar strategy of inhibiting or otherwise decreasing a donor cells' MHC I expression is unlikely to provide a singular solution to allograft rejection due to the phenomenon of "missing-self recognition" by NK cells. For example, incomplete protection from allograft rejection via reduction of MHC-I expression in the transplant is seen in *Kidney International*, Vol. 62 (2002), pp. 290-300. In addition, NK cells, unlike CD8+ cytotoxic cells, can kill target cells producing insufficient levels of cell surface MHC-I without MHC restriction. NK cell activation is dependent on a complex and integrated balance of signals from both activating and inhibitory receptors on the cell surface, and because target cells expressing insufficient levels of MHC-I do not provide sufficient inhibitory signals through MHC-I expression, they are often destroyed. Due to the limited expression of MHC-II throughout the body and its specialized role in immune responses, a similar NK cell-based strategy for identification of cells that demonstrate altered or decreased MHC-II expression has not yet been identified and should be considered only for grafts which express HLA class II (e.g. hematopoietic stem cells).

In yet another known approach of preventing tissue rejection, recipient allo-activated regulatory T cells can be generated ex vivo and are then introduced into a recipient before transplantation. Donor antigen is introduced into the recipient after transplantation to boost recipient regulatory T cells as described in US20060292164A1. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. While such approach may circumvent at least some of the above problems, other difficulties still remain. Most notably, such method may still not overcome problems with tissues having HLA-type mismatch.

Thus, even though various approaches are known in the art to reduce allograft recognition and rejection, several drawbacks still remain. Therefore, there is still a need for compositions, cells, and methods to reduce allograft recognition and rejection.

SUMMARY OF THE INVENTION

The inventive subject matter is directed to various cells, compositions, and methods of reducing CD8$^+$ and NK cell detection of cells or tissues to thereby reduce allograft recognition and rejection allograft. Most preferably, native HLA expression of the cell or tissue is reduced to so avoid or reduce CD8$^+$ cell detection, and the cell or tissue is further genetically modified to express the host matched HLA and/or expression of HLA-E, F or G and/or CMV-UL-18 to so reduce NK cell recognition.

For example, donor cells or tissue may be genetically modified to inhibit the expression of endogenous (32 microglobulin (B2M) and associated MHC I expression (e.g., via antisense or interfering RNA or genomic editing) to so inhibit CD8+ T cell recognition of allografts, and/or be further modified to express a B2M-HLA-G or HLA-E fusion protein (that is preferably unable to partner with the host's HLA-A, B, C) to so inhibit NK cell activation via the hosts "missing self" pathways. In another example, donor tissue may also be genetically engineered by reducing or abrogating expression of one or more of its original HLA-alleles and/or by recombinant expression of HLA-alleles that are identical or near-identical to the recipient HLA-type. For example, genomic editing may be employed to replace donor MHC-domains with recipient MHC-domains.

In one particularly preferred aspect of the inventive subject matter, a method of treating a donor cell or tissue having an originally expressed HLA-type is contemplated that includes a step of treating the cell or tissue such that at least some of the treated cell or tissue has a reduced or abrogated expression of the originally expressed HLA-type, wherein the reduced or abrogated expression is sufficiently low to reduce CD8+ detection. Such methods will also include a further step of genetically engineering the treated cell or tissue such that the engineered cell or tissue expresses at least one of (a) a recipient HLA-type, (b) a HLA-E, -F, and/or -G, optionally as a fusion protein comprising a β-2m portion, and (c) a CMV UL-18, optionally as a fusion protein comprising a β-2m portion. Most typically, expression of (a), (b), or (c) is sufficient to reduce NK cell recognition.

In further aspects of the inventive subject matter, the cell or tissue is treated with an inhibitor of MHC I antigen presentation, and suitable inhibitors of MHC I antigen presentation may include proteasome inhibitors and inhibitors of MHC I antigen expression (e.g., shRNA, siRNA, miRNA, or a regulatory proteins). Alternatively, or additionally, the step of treating the cell or tissue may also include a step of mutating or down-regulating expression of at least of β-2m, HLA-A, -B, and -C.

To overcome 'missing self' recognition by NK cells, the cell or tissue is further genetically engineered to express the recipient HLA-type, to express (the optional fusion protein comprising the β-2m portion and) the HLA-E, -F, and/or -G, and/or to express (the optional fusion protein comprising the β-2m portion and) the CMV UL-18. While not limiting to the inventive subject matter, it is typically preferred that the engineered cell is a stem cell, a cytotoxic T-cell, or a NK cell.

Consequently, the inventors also contemplate a genetically modified donor cell that includes a recombinant nucleic acid that is configured to express at least one of (a) a recipient HLA-type, wherein the expressed recipient HLA-type is different from an HLA-type of the donor cell before genetic modification, (b) a HLA-E, -F, and/or -G, optionally as a fusion protein comprising a β-2m portion, and (c) a CMV UL-18, optionally as a fusion protein comprising a β-2m portion. Most typically, expression of (a), (b), or (c) is sufficient to reduce NK cell recognition. Moreover, contemplated cells are further treated or modified to have a reduced or abrogated expression of the HLA-type of the donor cell before genetic modification, wherein the reduced or abrogated expression is sufficiently low to reduce CD8+ detection.

For example, the donor cell may be treated or modified to include or express an inhibitor of MHC I antigen presentation (e.g., siRNA, an shRNA, an miRNA, or a regulatory protein) and/or may have a deletion or substitution of a nucleic acid that encodes the HLA-type of the donor cell before genetic modification. To avoid 'missing self' recognition by NK cells, the recombinant nucleic acid in the genetically modified donor cell may be configured to express the recipient HLA-type, (the optional fusion protein comprising the β-2m portion and) the HLA-E, -F, and/or -G, and/or (the optional fusion protein comprising the β-2m portion and) the CMV UL-18.

While not limiting to the inventive subject matter, it is contemplated that the genetically modified donor cell may be a stem cell, a cytotoxic T-cell, or a NK cell (which may be further modified to have a reduced or abolished expression of at least one killer cell immunoglobulin-like receptor (KIR), to express a high-affinity Fcγ receptor, and/or to express a chimeric T-cell receptor.

Various objects, features, aspects and advantages of the inventive subject matter will become more apparent from the following detailed description of preferred embodiments, along with the accompanying drawing figures in which like numerals represent like components.

DETAILED DESCRIPTION

Figures 1A, 1B, 2A:
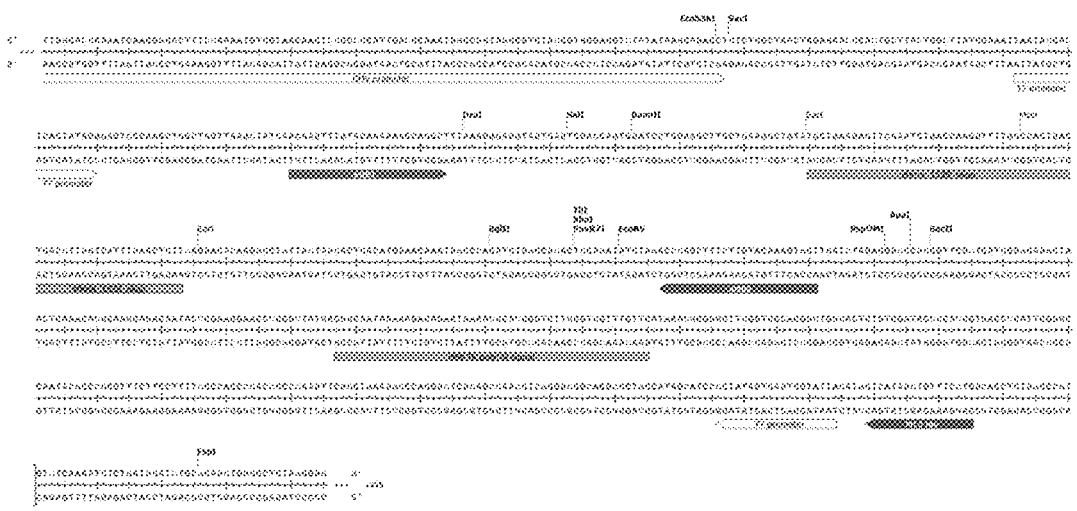
FIG. 1A shows the sequence for human β-2 microglobulin mRNA with the peptide encoding portion in bold face and an shRNA target sequence with underline.
FIG. 1B shows an exemplary nucleotide sequence for a plasmid encoding a DNA that, when transcribed, forms a short hairpin RNA targeting the '1528' shRNA target sequence.
FIG. 2A shows the shRNA '1528' sequence and a control sequence.

The inventors have discovered that allograft recognition and/or rejection of donor cells in a non-donor host organism can be significantly reduced, if not even entirely avoided by a genetic modification of the donor cell or tissue in which expression of the major histocompatibility class I (or MHC-I) proteins of the donor cell is suppressed to escape the host's CD8+ cytotoxic T cell response, and in which one or more inhibitory factors are expressed that enable the donor cell to escape from host natural killer (NK) cell-mediated lysis. Inhibitory factors include factors known to reduce, counteract, or otherwise inhibit NK cell activation and may be naturally occurring or synthetic entities (e.g., host MHC-I molecules, or fusion molecules between a β-2m portion and a HLA-E, -F, and/or -G portion, and/or a CMV UL-18 portion).

Therefore, and viewed from a higher perspective, expression of endogenous HLA-A, -B, or -C of donor cells can be reduced or inhibited using (1) pharmacological inhibitors of MHC I antigen presentation (e.g., proteasome inhibitors like bortezomib, etc), (2) expression of shRNA, siRNA, miRNA or to thereby target endogenous untranslated regions of mRNA encoding β-2m, HLA-A, -B, or -C, or other proteins involved in MHC-I antigen presentation, (3) genomic alteration or deletion of the genes encoding β-2m, HLA-A, -B, and/or -C or other proteins involved in MHC-I antigen presentation, and/or (4) expression of proteins which downregulate or otherwise inhibit MHC-I expression (e.g., ICP47, etc). So treated or modified donor cells are then further rendered impervious to NK cell recognition through the expression of one or more inhibitory factors, including cDNAs encoding HLA-A, -B, or -C matching the recipient's HLA-A, -B, and/or -C (with or without altered UTR sequences), cDNAs encoding an untranslated sequence-less β-2m that is fused to HLA-E, -F, and/or -G (e.g., via a glycine/serine linker), and/or cDNAs encoding an untranslated sequence-less β-2m that is fused to CMV UL-18.

Of course, it should be appreciated that the reduction of expression of endogenous HLA-A, -B, or -C of donor cells and the expression of one or more inhibitory factors can be achieved in a single modification in which genomic editing techniques are employed that swap out the expressed HLA-type for a nucleic acid encoding the inhibitory factors as is also further described in more detail below.

For example, in one preferred exemplary aspect the inventive subject matter, a donor cell is obtained from a cell culture and the originally expressed HLA-type is determined (e.g., NK92 cell with HLA-type HLA-A*02:151:01:02L) for the cell. Most preferably, the HLA-typing is performed using whole genome, exome, and/or transcriptome sequencing and sequence analysis is preferably performed using De Bruijn graph methodology as is further described in more detail in our copending US provisional application with the Ser. No. 62/209,858, filed 25-Aug.-15. Of course, it should be appreciated that other methods of HLA-typing are also deemed suitable for use herein. Regardless of the manner of HLA-typing, it is preferred that the donor cell is then genetically modified to reduce or abrogate expression of the expressed HLA-type, preferably via transcription of a recombinant nucleic acid to so produce a small hairpin RNA (shRNA) that is then processed in the cell (via Drosha and Dicer) to ultimately form a small interfering RNA (siRNA) that targets the RNA encoding the expressed HLA-type via the RNA-induced silencing complex (RISC). Most typically, expression of the shRNA is achieved from a viral vector (e.g., via adenovirus or adeno-associated virus) following protocols well known in the art. Using the appropriate choice of the shRNA as is further described in more detail below, expression of the HLA-type of the donor cell can be reduced or even abrogated such that the so modified donor cells exhibit reduced or even completely abolished CD8+ detection.

Thusly treated cells are then further subject to genetic engineering to force the cells to express an inhibitory factor that protects the engineered cells from NK attack (triggered due to lack of sufficient levels of MHC-I complex, 'missing self' rejection). While conceptually various manners of NK inhibition are deemed suitable, it is generally preferred that the engineered cells are transfected to express a fusion protein that comprises a β-2m portion and a HLA-E, -F, and/or -G portion, linked together via a preferably short flexible linker (e.g., G4S linker). Typically, such chimeric protein is not able to associate with other HLA components, but will be expressed at a level effective to reduce or even completely abolish NK cell activation.

With respect to contemplated donor cells and tissues it should be noted that all cells and tissues, and particularly mammalian cells and tissues are deemed suitable for use herein. For example, suitable cells may have human, ape, monkey, porcine, or rodent origin and may be primary cells or cultured cells. With respect to the cell type, it should be noted that all cell types are contemplated herein, however, preferred cells types include ectodermal, mesodermal, and endodermal stem cells, progenitor cells and blast cells of at least pluripotent character. For example, suitable cells include bone marrow stem cells and adult reserve stem cells. Likewise, suitable cells also include those belonging to the immune system, and particularly preferred cells include B-cells, cytotoxic T-cells, and NK cells, all of which may be genetically modified. For example, modified NK cells may be engineered to have a reduced or abolished expression of at least one killer cell immunoglobulin-like receptor (KIR), may express one or more high-affinity Fcγ receptor, and/or may express a chimeric T-cell receptor.

On the other hand, and especially where the genetic modification of a donor cell is done on an embryonic stem cell, such modified cells can be implanted into a blastocyst to ultimately give rise to a transgenic organism that may then serve as a source of cells and/or tissues or organs having reduced or abrogated expression of the originally expressed HLA-type and/or that may express one or more inhibitory factors as also addressed further below. Thus, it should be appreciated that the cells and tissues with reduced or abrogated expression of the originally expressed HLA-type may be primary cells or tissues, or cultured cells or tissues. Moreover, and depending on the type of cell of tissue employed, various uses of the treated and genetically modified cells are contemplated, including therapeutic uses to reinstate lost function (e.g., Langerhans cells or pancreatic tissue for type-I diabetics) or drug-like use (e.g., NK92 cells for cancer immunotherapy), or stem cells for treatment of inflammatory conditions.

Determination of the originally expressed HLA-type can be done in numerous manners, and all known manners are deemed suitable for use herein. Thus, suitable methods include serological methods using HLA-specific antibodies as well as genetic methods using genome sequencing, PCR-based methods, etc. However, especially preferred manners of HLA-typing include genomic computational methods in which the correct haplotypes are predicted using De Bruijn graph methodology as is described in more detail in copending US provisional application with the Ser. No. 62/209,858, filed 25-Aug.-15.

Once identified, expression of the originally expressed HLA-type can be reduced or even entirely abrogated in various manners. For example, and as already described above, expression can be reduced or eliminated by down-regulation of a component of the MHC-I protein complex, and most preferably the β-2m component. As further described in more detail below, expression can be down-regulated via a recombinant nucleic acid that, when transcribed, gives rise to a RNA species that directly or indirectly leads to degradation of the RNA encoding the originally expressed HLA-type. For example, a recombinant nucleic acid may be introduced into the donor cell via viral transfer, electroporation, transfection, etc., and it should be noted that the imported recombinant nucleic acid may be integrated into the donor cell genome, or may be maintained in an extrachromosomal manner.

Most typically, the recombinant nucleic acid will contain a promoter element that may be constitutively active, or that may be responsive to a tissue specific environment or that may be inducible with a specific inducer. Regardless of the specific regulation, it should be appreciated that the recombinant nucleic acid will give rise to a transcript that will specifically interfere with the transcription and/or translation of the nucleic acid that encodes the originally expressed HLA-type. For example, the transcript may be an antisense RNA that hybridizes to the nucleic acid that encodes the originally expressed HLA-type, or may be a shRNA, miRNA, or siRNA that will lead to RNA interference via the RISC complex. There are numerous gene silencing methods known in the art, and all of those are deemed suitable for use herein. Alternatively, it should be noted that the gene that encodes the originally expressed HLA-type may also be mutated to so result in a non-functional HLA, and mutations are preferably performed in a site specific manner.

Where desired, it should further be recognized that silencing of the gene that encodes the originally expressed HLA-type may also be performed by replacement of at least a portion of the gene for the HLA-type with another nucleic acid using genome editing tools well known in the art. For example, replacement of the expressed HLA-type of the tissue with another nucleic acid may be performed using knock-in/knock-out mutagenesis, hit-and-run-targeting, zinc finger-based genome editing, CRISPR-Cas9 genome editing, or TALE genome editing.

In that context, it should be particularly appreciated that the newly integrated nucleic acid may not only abrogate expression of the originally expressed HLA-type, but may also be used to provide a second functional component to the donor cell. Most preferably, the second functional component will lead to the expression of an inhibitory factor that reduced or eliminates NK cell activation (due to reduced or no MHC-complex on the donor cell). Consequently, and among other suitable inhibitory factors, particularly preferred inhibitory factors include (a) a recipient HLA-type, (b) a fusion protein comprising a β-2m portion and a HLA-E, -F, and/or -G portion, and/or (c) a fusion protein comprising a β-2m portion and a CMV UL-18 portion. Thus, and where option (a) is employed, NK cell activation via 'missing self' is avoided by presentation of the recipient's HLA-type, which advantageously also avoids CD8+ based recognition and rejection. Alternatively, where option (b) is employed, NK cell activation is avoided by presentation of the HLA-E, -F, and/or -G portion that is known to reduce NK cell activation. Most preferably, the HLA-E, -F, and/or -G portion will be covalently fused to at least a portion of the β-2m protein to provide a membrane anchor and binding partner to the β-2m protein. Typically, fusion is performed as a chimeric protein, most preferably using a short and flexible linker moiety having between 5 and 50 amino acids (e.g., $[G_4S]_n$, etc.). Further suitable linkers are described elsewhere (see e.g., Protein Engineering, Design & Selection vol. 27 no. 10 pp. 325-330, 2014). Similarly, where option (c) is employed, NK cell activation may be avoided by presentation of a viral inhibitory factor (e.g., CMV UL-18, HSV ICP47) known to reduce NK cell activation. Of course, it should also be appreciated that while fusion proteins with a β-2m protein are generally preferred, expression of the inhibitory factors may also omit the β-2m portion and instead only present the inhibitory molecule (e.g., HLA-E, -F, -G, and/or UL-18 alone, optionally with membrane or transmembrane anchor).

Of course, it should also be appreciated that the expression of an inhibitory factor that reduces or eliminates NK cell activation (due to reduced or no MHC-complex on the donor cell) may also be performed from an independently introduced nucleic acid (rather than replacement of a sequence), and all manners of introduction of recombinant nucleic acids are deemed suitable for use herein, including viral transfection, lipofection, ballistic transfection, electroporation, and cell fusion. Likewise, it should be noted that all configurations of nucleic acids are deemed appropriate and include viral vectors, plasmids, phagemids, yeast artificial chromosomes, linear DNA, etc., and the person of ordinary skill in the art will readily be able to choose the proper configuration depending on the particular cell type and transfection method.

Alternatively, where it is desired to only temporarily reduce MHC-I expression on the donor cell without genetic manipulation, it should be appreciated that various pharmaceutical methods are also contemplated for use herein. For example, donor cells may be treated with compounds that inhibit protein processing and so indirectly inhibit or reduce MHC-I presentation on the cell surface. Among other suitable compounds, proteasome inhibitors may be employed, including bortezomib, bortezomib analogs, lactacystin, carfilzomib, or salinosporamide A. Similarly, TAP (Transporter associated with antigen) inhibitors such as ICP47, BNLF2a, or UL49.5 may be used to prevent HLA assembly, and/or taspasin inhibitors (e.g., US3, E3-19k) may be used to prevent proper MHC-I presentation.

Consequently, and viewed form a different perspective, the inventors also contemplate a genetically modified donor cell that comprises a recombinant nucleic acid configured to express at least one of (a) a recipient HLA-type, wherein the expressed recipient HLA-type is different from an HLA-type of the donor cell before genetic modification; (b) a fusion protein comprising a β-2m portion and a HLA-E, -F, and/or -G portion; and (c) a fusion protein comprising a β-2m portion and a CMV UL-18 portion. As noted above, it is generally contemplated that expression of the above components in sufficient to reduce NK cell activation. Moreover, contemplated cells will also be treated or genetically modified to have a reduced or abrogated expression of the HLA-type of the donor cell before genetic modification, wherein the reduced or abrogated expression is sufficiently low to reduce CD8+ detection. Consequently, such cells are thought to be less or even not recognized by the host immune system and particularly by the CD8+ and CD4+ cells and can therefore be employed as cell-based therapeutic entities.

EXAMPLES

As is shown in the following, cells were transfected with an expression plasmid to produce a transcript for an shRNA that ultimately gives rise to RNA interference, effectively reducing or even abrogating expression of the donor cell's native MHC-I complex by reduction of the β-2m portion.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Figure 2B:
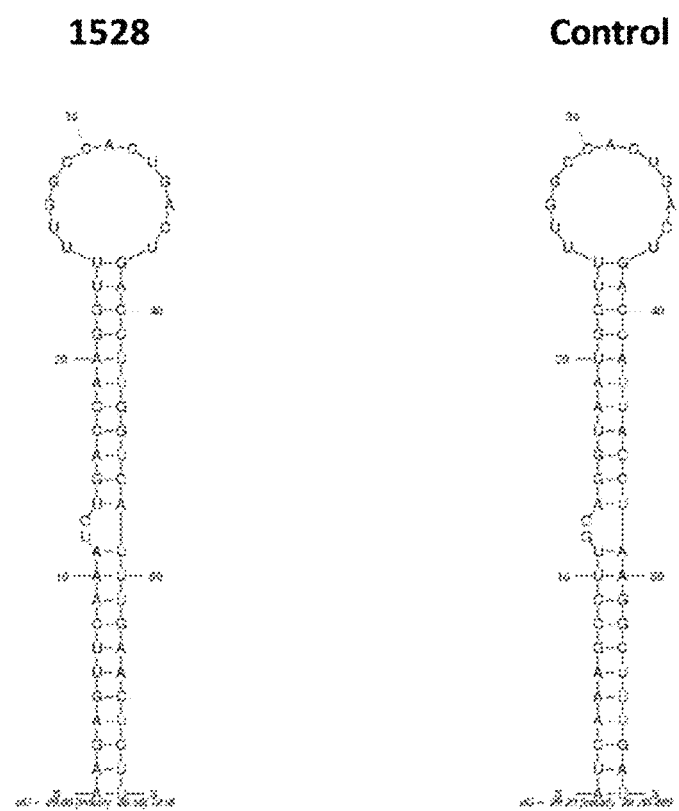
FIG. 2B illustrates structural predictions for the sequences of FIG. 2A with shRNA '1528' sequence on the left and a control sequence on the right.
Figure 2C:
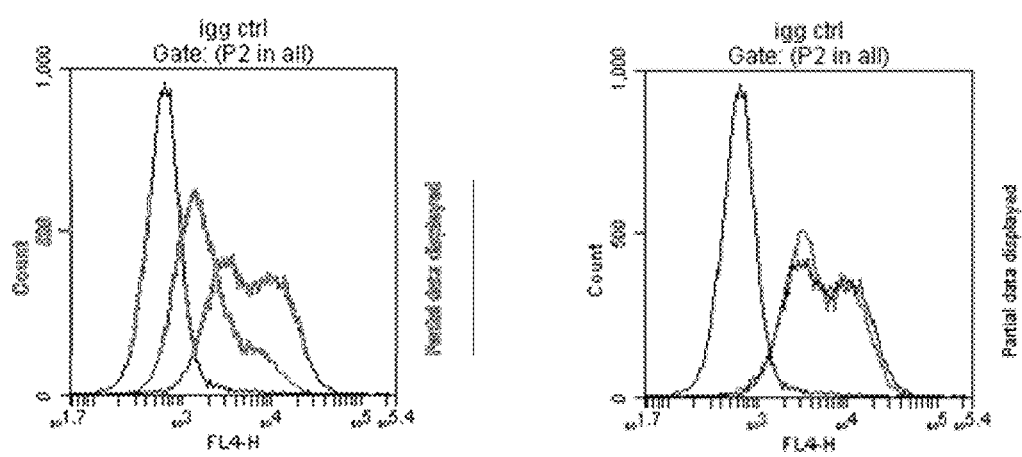
FIG. 2C shows exemplary cell analyses for cells with knockdown of human b2M.

FIG. 1A exemplarily depicts the human β-2 microglobulin mRNA sequence (SEQ ID NO. 1) in which the bold face portion denotes the protein coding portion and in which the underlined portion is the shRNA target sequence (also identified as '1528') present in the 3'untranslated region of the human β-2 microglobulin mRNA. Effectiveness of significant reduction in human MHC I expression was confirmed using a pan-HLA A, B, C antibody. FIG. 1B shows a portion of an exemplary plasmid (SEQ ID NO. 4), which when transcribed, forms a short hairpin RNA targeting the '1528' shRNA target sequence. Here, transcription is driven from the CMV promoter and will result in formation of a RNA that includes the shRNA targeting sequence. FIG. 2A provides a more detailed and linear view of the human β-2 microglobulin shRNA sequence ('1528') (SEQ ID NO. 2) and a corresponding control sequence (SEQ ID NO. 3) directly below, while FIG. 2B illustrates calculated secondary structures for the same sequences. Verification of the gene knockdown using the '1528' targeting sequence is presented in FIG. 2C. As can be observed in the left panel of FIG. 2C, the level of HLA-ABC expression of surface expression in untransfected cells (rightmost track) is decreased significantly when cells are transfected with the pcDNA_62GW_mir_1528 plasmid (middle track) nearly approaching the background non-specific binding achieved with isotype control antibody (leftmost track). In comparison, the right panel in FIG. 2C demonstrates that cells similarly treated but with control shRNA plasmid do not display meaningful inhibition of HLA-ABC expression.

More specifically, human Embryonic Kidney (HEK) 293T cells (ATCC, Manassas Va.) were seeded in a 12 well plate at a density of 1.5×105 cells/well in Dulbecco's modified eagle medium (Corning, Tewksbury Md.). On the following day, cells were transfected with 1 µg of either purified pcDNA_62GW_miR_1528 or control shRNA plasmid DNA (Qiagen, Valencia Calif.) using Lipofectamine 2000 per manufacturer's recommendations (Thermofisher, Waltham Mass.). Two days after transfection, the cells were harvested and incubated with APC-conjugated anti-human HLA-ABC or isotype control antibody (eBioscience, San Diego Calif.) prior to being evaluated on a Accuri C6 Flow cytometer with accompanying system software (BD Biosciences, San Jose Calif.).

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of reducing allograft recognition or rejection of an allograft by a recipient, comprising steps of:
   (a) determining the originally expressed HLA-type of 1) a donor cell or tissue and 2) a recipient;
   (b) treating the donor cell or tissue such that at least some of the treated donor cell or tissue has a reduced or abrogated expression of the originally expressed HLA-type, wherein expression of the originally expressed HLA-type is reduced or abrogated by treating the donor cell or tissue with an effective preparation comprising shRNA, siRNA or miRNA, and wherein the reduced or abrogated expression is sufficiently low to reduce an immune response by CD8$^+$ T cells of the recipient; and
   (c) genetically engineering the treated donor cell or tissue such that the engineered cell or tissue expresses at least one of
   (a) HLA-type of the recipient;
   (b) HLA-E, -F, and/or -G, alone or as a genetic fusion protein comprising β-2 microglobulin (β-2m); and
   (c) human cytomegalovirus UL-18 (CMV UL-18), alone or as a genetic fusion protein comprising β-2m; wherein expression of (a), (b), or (c) is sufficient to reduce natural killer (NK) cell activation; and transplanting the genetically engineered donor cell or tissue to the recipient.

2. The method of claim 1 wherein the step of determining the donor and recipient HLA types is performed using a genomic computational method, which predicts a correct haplotype using De Bruijn graph methodology.

3. The method of claim 1 wherein the step of determining the donor and recipient HLA types is performed using a serological method using HLA-specific antibodies, a genetic method using genome sequencing, or a PCR-based method.

4. The method of claim 1 wherein the step of treating the donor cell or tissue comprises mutating or down-regulating expression of at least of β-2m, HLA-A, -B, and -C.

5. The method of claim 1, wherein the engineered cell or tissue expresses the recipient HLA-type.

6. The method of claim 1, wherein the engineered cell or tissue expresses the fusion protein comprising the β-2m and the HLA-E, -F, and/or -G.

7. The method of claim 1, wherein the engineered cell or tissue expresses the fusion protein comprising the β-2m and the CMV UL-18.

8. The method of claim 1, wherein the engineered cell is a stem cell.

9. The method of claim 1, wherein the engineered cell is a cytotoxic T-cell or NK cell.

10. The method of claim 1 wherein the treated donor cell has a deletion or substitution of a nucleic acid that encodes the HLA-type of the donor cell before genetic modification.

11. The method of claim 1 wherein the donor cell or tissue is an NK cell that is further modified to
    (a) have a reduced or abolished expression of at least one killer cell immunoglobulin-like receptor (KIR);
    (b) express a high-affinity Fcγ receptor; or
    (c) express a chimeric T-cell receptor.

12. The method of claim 1 further comprising monitoring the recipient's reaction to the transplanted cells or tissue after transplanting genetically engineered donor cell or tissue.

13. The method of claim 1, wherein the recipient is a human being.

14. The method of claim 1, wherein the donor cell or tissue is derived from an animal other than a human being.

* * * * *